United States Patent [19]

Parins et al.

[11] Patent Number: 5,013,312

[45] Date of Patent: May 7, 1991

[54] BIPOLAR SCALPEL FOR HARVESTING INTERNAL MAMMARY ARTERY

[75] Inventors: David J. Parins, White Bear Lake; Gerald S. Szczech, Minnetonka; Demitre M. Nicoloff, Edina; Steven W. Berhow, Brooklyn Center, all of Minn.

[73] Assignee: Everest Medical Corporation, Minneapolis, Minn.

[21] Appl. No.: 495,405

[22] Filed: Mar. 19, 1990

[51] Int. Cl.[5] ............................................. A61B 17/39
[52] U.S. Cl. ...................................... 606/37; 606/39; 606/40; 606/48; 606/50
[58] Field of Search ..................... 606/27-29, 606/32, 34, 37, 39, 40, 41, 45, 46, 48-50, 129, 159, 167, 169, 170, 171

[56] References Cited

U.S. PATENT DOCUMENTS

| | | | |
|---|---|---|---|
| 4,646,738 | 3/1987 | Trott | 606/170 |
| 4,674,498 | 6/1987 | Stasz | 606/48 |
| 4,802,476 | 2/1989 | Noevenberg et al. | 606/48 |
| 4,850,353 | 7/1989 | Stasz et al. | 606/37 |
| 4,903,696 | 2/1990 | Stasz et al. | 606/37 |
| 4,922,903 | 5/1990 | Welch et al. | 606/37 |

Primary Examiner—Stephen C. Pellegrino
Assistant Examiner—Steven J. Shumaker
Attorney, Agent, or Firm—Haugen and Nikolai

[57] ABSTRACT

An bipolar electrosurgical instrument especially designed especially for use in freeing and rerouting of the internal mammary artery during coronary bypass surgery. It comprises a rigid pen-like handle having appropriate cut and coag control switches mounted thereon and a bendable tubular extension projecting from the distal end of the handle member. Mounted on the distal end of the extension is a blade holder designed to contain an ultrasonic transducer as well as the proximal end of the blade itself. The blade comprises a ceramic substrate having a pattern of metallization thereon defining a bipolar cutting gap along the side and end edges of the blade and a bipolar coagulating gap located inwardly from the side and end edges. A cable is used to join the implement to an electrosurgical generator and the individual wires in the cable extend through the pen-like body, the tubular extension and into the blade holder where electrical connections are made to the electrodes on the blade itself. By providing the bendable extension, the angle of the blade relative to the pen-like handle can be adjusted to accommodate the surgeon's angle of attack relative to the retracted chest wall.

14 Claims, 2 Drawing Sheets

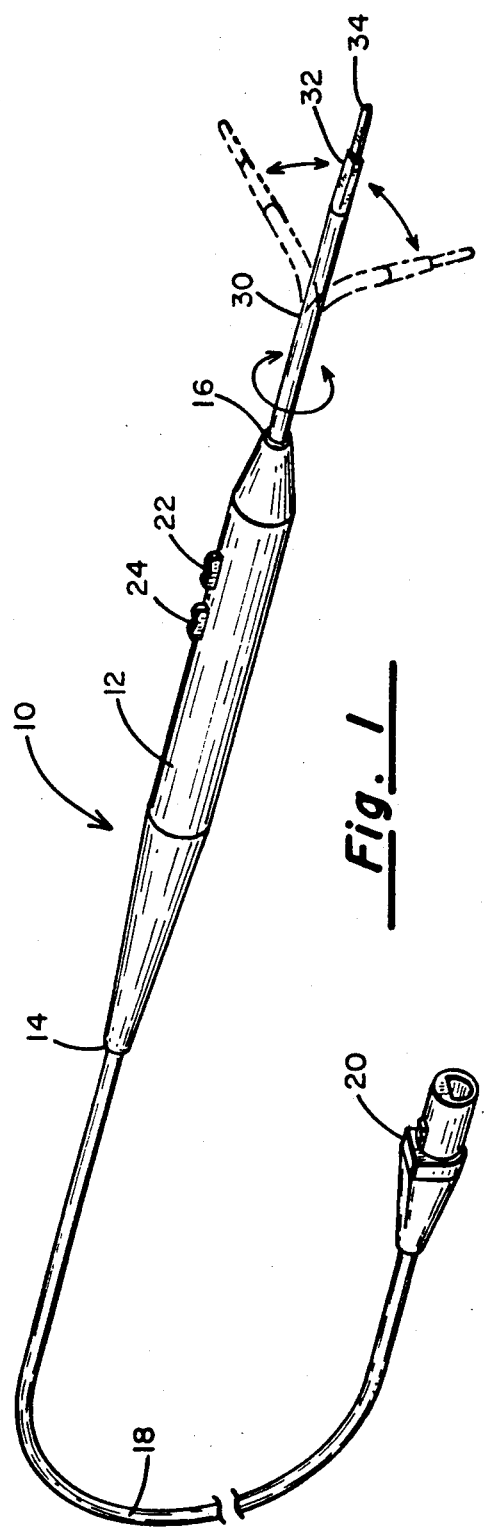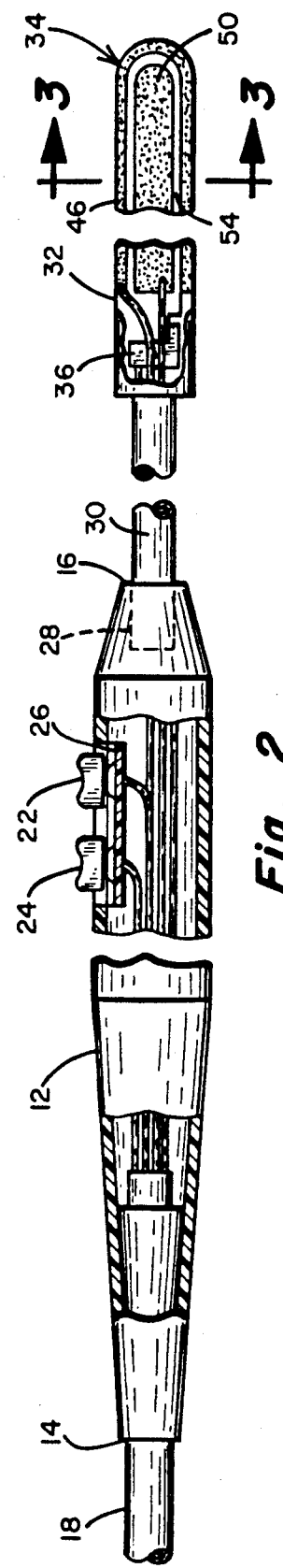

BIPOLAR SCALPEL FOR HARVESTING INTERNAL MAMMARY ARTERY

BACKGROUND OF THE INVENTION

I. Field of the Invention:

This invention relates generally to electrosurgical apparatus and more particularly to an electrosurgical instrument for facilitating the severing of the internal mammary artery for use in coronary bypass surgery.

II. Discussion of the Prior Art:

In performing one form of a coronary bypass surgical procedure, a segment of a blood vessel harvested from another portion of the body is used as an autogenous graft to effectively bypass a stenosed segment of a coronary artery to restore adequate blood flow distal of the blockage. In such procedure, a segment of the saphenous vein is stripped from the patient's leg and subsequently used as the bypass graft. In a significant number of cases, the resulting wound to the leg is slow to heal and a cause of considerable pain and irritation.

Rather than harvest the saphenous vein, surgeons have also utilized the internal mammary artery which depends from the long thoracic artery behind the first and second rib. During open heart surgery, a thoracotomy is performed and the chest wall is retracted to provide access. The internal mammary artery is tucked beneath the upper rib cage and in order to sever the internal mammary artery from surrounding tissue, the surgeon must insert a scalpel at a particular angle to gain purchase to that artery. Once freed of surrounding tissue, the artery is cut and the free end is subsequently anastomosed to the coronary blood supply to the heart muscle. Moreover, because the internal mammary artery has a number of branches which must be cut and stapled, the procedure tends to result in a significant blood loss and, accordingly, prompt hemostasis is required.

The present invention comprises an electrosurgical instrument specifically designed for facilitating the severing of the internal mammary artery wile maintaining its condition to allow its severed end to be anastomosed to the diseased coronary artery distal of its stenosis. It comprises a pen-like handle having a proximal end and a distal end. Mounted on this handle are one or more control switches for controlling the application of RF energy to a blade member. The handle is arranged to be coupled through a cord or cable to an electrosurgical generator. Mounted in the distal end portion of the handle member is a bendable tubular segment which preferably is formed from a suitable metal that can be bent or shaped during use to a desired angular orientation without kinking. Mounted on the end of the bendable segment is a blade holder in the form of a molded plastic body having a cavity therein for containing a piezoelectric crystal and a socket for receiving the end of the blade member.

The blade member itself comprises an elongated thin insulating substrate, preferably a high temperature ceramic, which is beveled along its opposed edge and end surfaces. Electrodes in the form of metallic traces are then disposed on the substrate proximate the beveled edges so as to create a gap across the edge from a conductive trace on one major surface to an electrode on the opposite major surface. The blade may further include further electrodes centrally disposed on the substrate and spaced from the edge electrodes by a predetermined gap.

When the blade member is inserted in the socket in the blade holding member, a portion of the blade is in contact with the transducer and the transducer terminals as well as the electrode traces are coupled by conductors back through the bendable tube and through the hand to the cable.

In use, the surgeon may appropriately bend the tubular member on the end of the handle to an appropriate angle whereby the blade may be inserted beneath the retracted and raised chest wall and brought into engagement with the internal mammary artery. By depressing a first control switch on the handle, an RF voltage is applied not only across the cut electrodes, but also across the transducer's contacts so as to impart high frequency vibration of a very small stroke to the blade as it cuts through the tissue comprising the internal mammary artery. The flow of blood may be stemmed through coagulation by depressing a second handle control switch whereby the RF energy is applied between a cut electrode and a larger area coag electrode. Again, operation of the coag switch also results in energization of the piezoelectric crystal comprising the ultrasonic transducer. As is explained in the Stasz U.S. Pat. No. 4,674,498, the vibration of the blade during cutting and coagulation functions to maintain it relatively more free of charred tissue which might otherwise render the electrosurgical instrument less effective.

OBJECTS

It is accordingly a principal object of the present invention to provide an improved electrosurgical instrument for facilitating severing of the internal mammary artery of a patient for subsequent reattachment during coronary bypass surgery.

Another object of the invention is to provide an electrosurgical instrument in which the angular disposition of the cutting blade may be adjusted relative to a hand piece.

Yet another object of the invention is to provide an electrosurgical instrument for facilitating release and severing of the internal mammary artery which employs ultrasonic vibration of the cutting/coagulating blade during use.

A still further object of the invention related to the immediately foregoing object is the provision of an electrosurgical instrument wherein vibration of the blade during cutting and coagulation maintains the blade relatively free of charred tissue deposits which might otherwise adversely affect the performance of the instrument.

DESCRIPTION OF THE DRAWINGS

The foregoing features, objects and advantages of the invention will become more apparent to those skilled in the art from the following detailed description of a preferred embodiment, especially when considered in conjunction with the accompanying drawings in which like numerals in the several views refer to corresponding parts.

FIG. 1 is a perspective view of the preferred embodiment;

FIG. 2 is a longitudinal partial cross-sectional view of the instrument of FIG. 1;

DESCRIPTION OF THE PREFERRED EMBODIMENT

Figure 3:
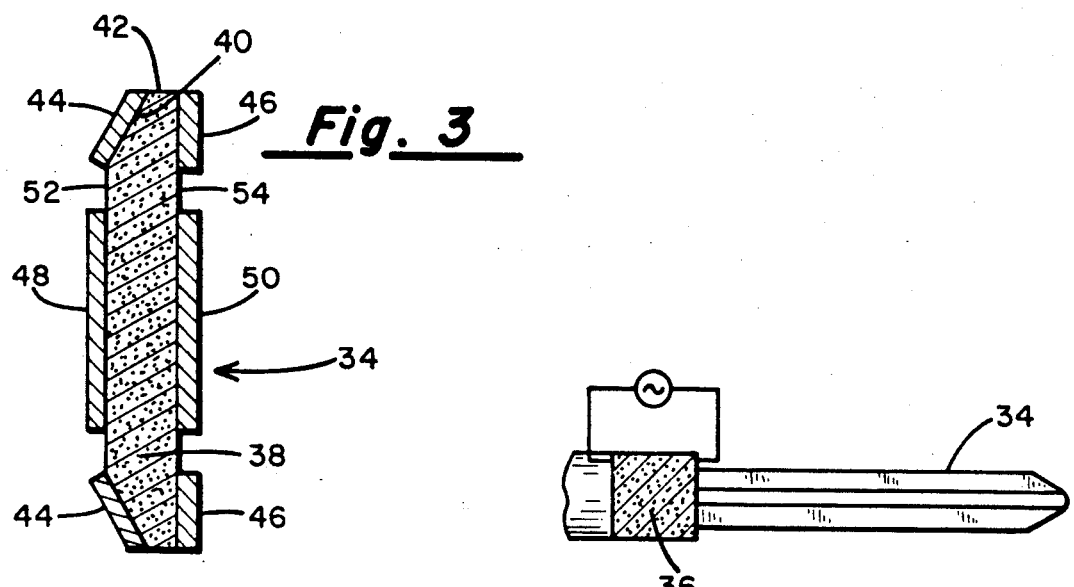
FIG. 3 is a cross-sectional view taken along the line 3—3 in FIG. 2.

Referring first to FIG. 1, there is illustrated generally by numeral 10 the presently preferred embodiment and best mode contemplated for implementing the electrosurgical instrument of the present invention. It is seen to comprise a rigid molded plastic pen-like handle 12 having a proximal end 14 and a distal end 16. Extending from the proximal end of the handle 12 is a flexible elongated electrical cable 18 which terminates in a connector 20 adapted to mate with the output jacks of an electrosurgical generator (not shown). The electrosurgical generator is capable of generating a radio frequency voltage and at a power level compatible with electrosurgical instruments of the type being described herein. One such device which may be employed is that disclosed in the Stasz et al application Ser. No. 07/254,203, filed Oct. 6, 1988, and entitled "ELECTROSURGICAL GENERATOR".

With reference to FIGS. 1 and 2, it is to be noted that appropriately affixed to the molded plastic handle member 12 is a set of push-button control switches including a switch 22 labeled "cut" and a switch 24 labeled "coag". The switches are wired through conductors in the cable 18 to the electrosurgical generator and when depressed will result in appropriate RF potentials being delivered to the electrodes on the blade portion of the instrument 10 yet to be described The manner in which the switches and associated cable are configured may be discerned upon a reading of the Noerenberg et al. U.S. Pat. No. 4,802,476, entitled "ELECTRO-SURGICAL INSTRUMENT" and assigned to applicant's assignee. As is disclosed in that patent, the push-buttons cooperate with so-called membrane or diaphragm switches disposed on a printed circuit card 26 mounted directly beneath the push-buttons to deliver control signals to the generator.

Fitted into a cylindrical bore 28 formed in the distal end 16 of the pen-shaped handle 12 is a bendable tubular extension 30. The member 30 is preferably formed from a malleable material such as annealed stainless steel and may be coated with a layer of a suitable plastic such as silicon rubber to provide electrical insulation thereto. As is illustrated by the dotted line representations in FIG. 1, by providing a soft malleable tubular segment 30, the end portion thereof can be bent by the physician at a desirable angle and that angle will be retained in use.

Disposed on the distal end of the extension member 30 is a blade holder 32 which is adapted to receive and firmly clamp the proximal end of the blade member 34. Also contained within the blade holder 32 is a piezoelectric crystal 36 which appropriately abuts the blade and which, when energized by a suitable source of high frequency voltage, imparts ultrasonic vibration to the blade 34.

FIG. 3 is a greatly enlarged cross-sectional view of the blade taken along the line 3—3 in FIG. 2. The blade 34 is seen to comprise a thin ceramic substrate 38 which is generally flat except for a bevel 40 formed on one side surface of the substrate proximate the peripheral edge thereof. Ceramics such as silicon nitride and aluminum nitride have been found quite suitable for the substrate. Rather than sloping to a fine line, the edge of the blade is back ground to create a blunt edge 42. The ceramic substrate is then metallized by plating, spraying or otherwise depositing conductive metal strips 44 and 46 on opposed side surfaces of the substrate proximate the blunt edge 42. The edge 42 is free of metallization and constitutes a bipolar cut gap.

A further pair of electrodes including segments 48 and 50 are likewise adhered to the opposed side surfaces of the substrate 38 and are spaced from the bipolar cut electrodes 44 and 46 by gaps 52 and 54. The gap 42 between the cut electrodes 44 and 46 may typically be .005 inches and when a RF voltage is applied across these two electrodes, an arc is created as the cut gap 42 is brought into contact with tissue to be severed. The gaps 52 and 54, however, are slightly wider, e.g., 0.010 inches and when an appropriate RF voltage is established between the electrode 48 and the electrode 44 or between electrode 50 and electrode 46, coagulation rather than cutting takes place.

The RF voltage for cutting and coagulation is fed through wires in the cable 18 which extend through the hollow handle portion 12, the tubular bendable extension 30 and the blade holder 36 and are electrically connected to the respective blade electrodes whereby a RF cutting voltage or an RF coagulation voltage is delivered from the electrosurgical generator (not shown) to the appropriate blade electrodes upon control signals being delivered to the electrosurgical generator from the push-button switches 22 and 24.

As is pointed out in the aforereferenced Stasz patent, by appropriately ultrasonically vibrating the blade during cutting and coagulation, a cavitation process is created in which tissue debris cannot effectively build up on the blade 34 to the point where the gaps become bridged by burnt-on debris which might otherwise detract from the ability of the instrument to cut and coagulate over prolonged time intervals without the need from mechanically removing the debris from the blade.

Figure 4A:
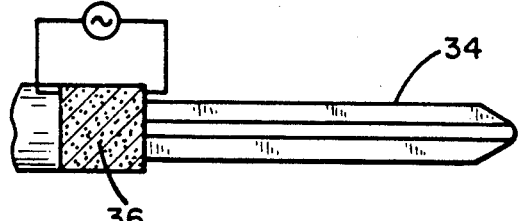
FIGS. 4a through 4d comprise partial cross-sectional views showing alternative ways of interfacing the blade portion of the instrument with an ultrasonic transducer.

The drawings of FIGS. 4a through 4d illustrate several different ways of mounting the piezoelectric crystal relative to the blade 34. In the view of FIG. 4a, the transducer 36 abuts the proximal end of the blade 34 to affect Y-mode (longitudinal) vibration of the blade.

Figure 4B:
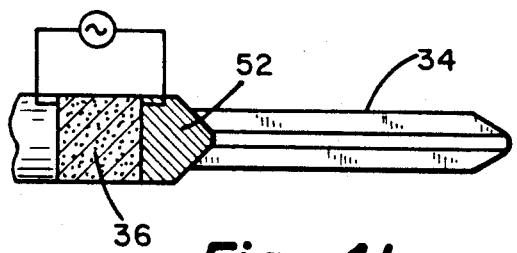

It has been found expedient to also employ an ultrasonic coupler 52 between the piezoelectric crystal 36 and the blade 34 as shown in FIG. 4b. The coupler is preferably formed from stainless steel or other material which exhibits low elasticity. By appropriately tapering the coupler 52 as shown in FIG. 4b, the vibrational energy delivered to the blade 34 is enhanced. The manner in which the coupler 52 and the blade 34 are joined in FIG. 4b results in a Y-mode (longitudinal) vibration of the blade.

Figure 4C:
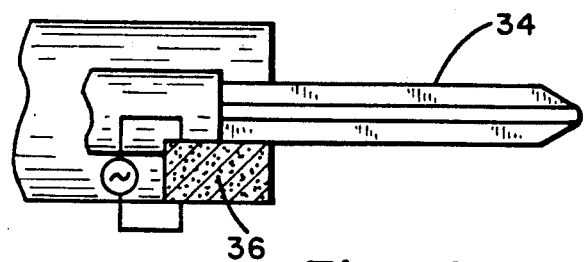
Figure 4D:
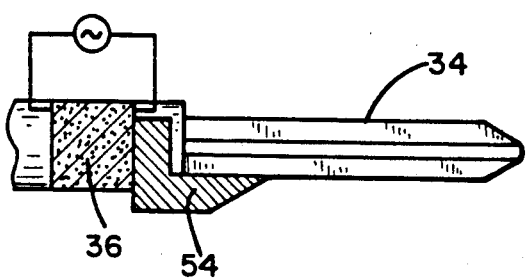

FIG. 4c illustrates the manner in which the piezoelectric crystal 36 may be made to abut a side edge of the blade with the crystal being oriented so as to produce Z-mode (transverse) vibrations of the blade.

FIG. 4d again incorporates an ultrasonic coupling member 54 between the blade 34 and the crystal 36 to enhance the Z-mode vibration of the blade.

In each instance, both the crystal 36 and the ultrasonic coupling member 52 or 54 is physically housed within the molded plastic blade holder member 32 where electrical connections are established between the terminals of the piezoelectric crystal and conductors extending through the cable 18 back to the electrosurgical generator.

As mentioned in the introductory portion of this specification, by providing the bendable extension 30, the physician may set the angle between the handle portion 12 and the blade so as to accommodate the angle at which the chest wall is retracted during use in stripping away tissue so as to free up the internal mammary artery for attachment to the particular coronary artery being bypassed. The bipolar nature of the cutting and coagulation electrodes obviates the need for a large-surface body plate and confines the flow of electric current only to those zones closely surrounding the cut gap 40 and the coagulation gaps 52 and 54.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the claims of the invention itself.

We claim:

1. An electrosurgical instrument for resectioning of an internal mammary artery comprising:
   (a) a rigid tubular handle member having a proximal end and a distal end, said handle including a longitudinal bore extending proximally from said distal end;
   (b) a bipolar blade member including an insulating substrate having at least one tapered working edge and first electrode means extending along said one working edge in spaced-apart orientation on opposed sides of said substrate to define a cut gap;
   (c) a bendable cylindrical metal tube having a proximal end inserted into said longitudinal bore and a distal end;
   (d) blade clamping means attached to said distal end of said metal tube for securing said blade member to said distal end of said metal tube;
   (e) ultrasonic transducer means disposed within said blade clamping means for mechanically driving said blade member; and
   (f) conductor means extending through said proximal end of said handle and through said cylindrical metal tube to said transducer means and said first electrode means for carrying electrical signals to said transducer means and to said first electrode means.

2. The electrosurgical instrument as in claim 1 wherein said blade member further includes second electrode means on said opposed sides of said substrate and spaced a predetermined distance from said first electrode means to form a bipolar coagulation gap.

3. The electrosurgical instrument as in claim 2 and further including switch means mounted on said handle member and in circuit with said conductor means for selectively controlling the application of a cut voltage across said cut gap and a coagulating voltage across said coag gap.

4. The electrosurgical instrument as in claim 1 wherein said cylindrical metal tube is an annealed stainless steel.

5. The electrosurgical instrument as in claim 4 wherein said metal tube is covered with a flexible electrically insulating material.

6. The electrosurgical instrument as in claim 1 wherein said insulating substrate is a member of the group of ceramics including silicon nitride and aluminum nitride.

7. The electrosurgical instrument as in claim 1 wherein said ultrasonic transducing means comprises a piezoelectric crystal having a pair of electrodes disposed thereon, said crystal directly abutting said blade member, and said pair of electrodes being coupled to said conductor means.

8. The electrosurgical instrument as in claim 1 wherein said ultrasonic transducing means comprises a piezoelectric crystal having a pair of electrodes disposed thereon coupled to said conductor means; and a vibration transmitting coupling member contacting said piezoelectric crystal and abutting said blade member for imparting vibrational energy to said blade member.

9. The electrosurgical instrument as in claim 7 or 8 wherein said blade member is vibrated along the longitudinal axis of said blade member.

10. The electrosurgical instrument as in claim 7 or 8 wherein said blade member is vibrated in a direction transverse to the longitudinal axis of said blade member.

11. An electrosurgical instrument for resectioning of an internal mammary artery comprising:
    (a) a rigid tubular handle member having a proximal end and a distal end, said handle including a longitudinal bore extending proximally from said distal end;
    (b) a bipolar blade member including an insulating substrate having at least one tapered working edge and first electrode means extending along said one working edge in spaced-apart orientation on opposed sides of said substrate to define a cut gap;
    (c) a bendable cylindrical metal tube having a proximal end inserted into said longitudinal bore and a distal end;
    (d) blade clamping means attached to said distal end of said metal tube for securing said blade member to said distal end of said metal tube; and
    (e) conductor means extending through said proximal end of said handle and through said cylindrical metal tube to said first electrode means for carrying electrical signals to said first electrode means.

12. The electrosurgical instrument as in claim 11 wherein said blade member further includes second electrode means on said opposed sides of said substrate and spaced a predetermined distance from said first electrode means to form a bipolar coagulation gap.

13. The electrosurgical instrument as in claim 12 and further including switch means mounted on said handle member and in circuit with said conductor means for selectively controlling the application of a cut voltage across said cut gap and a coagulating voltage across said coag gap.

14. The electrosurgical instrument as in claim 11 wherein said insulating substrate is a member of the group of ceramics including silicon nitride and aluminum nitride.

* * * * *